(12) United States Patent
Koch et al.

(10) Patent No.: US 8,460,628 B2
(45) Date of Patent: Jun. 11, 2013

(54) SPIRO COMPOUNDS

(75) Inventors: Matthias Koch, Wiesbaden (DE); Stefan Spange, Orlamuende (DE); Arno Lange, Bad Duerkheim (DE); Hans Joachim Haehnle, Neustadt (DE); Rainer Dyllick-Brenzinger, Neustadt (DE); Phillip Hanefeld, Heidelberg (DE); Marc Schroeder, Canton, MI (US); Illshat Gubaydullin, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 343 days.

(21) Appl. No.: 12/810,765

(22) PCT Filed: Dec. 1, 2008

(86) PCT No.: PCT/EP2008/010169

§ 371 (c)(1),
(2), (4) Date: Jun. 25, 2010

(87) PCT Pub. No.: WO2009/083083

PCT Pub. Date: Jul. 9, 2009

(65) Prior Publication Data

US 2010/0284882 A1 Nov. 11, 2010

(30) Foreign Application Priority Data

Dec. 27, 2007 (DE) .......................... 10 2007 063 284

(51) Int. Cl.
*C01B 33/20* (2006.01)
*C08G 77/00* (2006.01)
*C08J 9/26* (2006.01)
*C07F 7/00* (2006.01)

(52) U.S. Cl.
USPC ............... 423/325; 556/54; 556/464; 528/40; 521/61

(58) Field of Classification Search
USPC .......... 556/54, 464; 528/40; 521/61; 423/325
See application file for complete search history.

(56) References Cited

PUBLICATIONS

Mehrotra et al., Indian Journal of Chemistry, vol. 11, pp. 814-816 (1973).*
International Search Report of PCT/EP2008/010169 (Mar. 3, 2009).
Database CA [Online] Chemical Abstracts Service—Mehrotra, R. C. et al. "Reactions of Titanium and Zirconium Alkoxides with Salicylaldehyde" XP002517484 & Indian Journal of Chemistry, vol. 11, No. 8 (1973) pp. 814-816.
S. Grund et al., "Zwillingspolymerisation : ein Weg zur Synthese von Nanokompositen", Angew. Chem., vol. 119 (2007) pp. 636-640.

* cited by examiner

*Primary Examiner* — Porfirio Nazario Gonzalez
(74) *Attorney, Agent, or Firm* — Millen, White, Zelano & Branigan, P.C.

(57) ABSTRACT

The invention relates to spiro compounds of the formula (I) and to monolithic materials prepared therefrom by twin ring-opening polymerization which consist of a porous metal oxide or semimetal oxide framework and are suitable for use as catalyst supports or as supports for active compounds.

22 Claims, 2 Drawing Sheets

SPIRO COMPOUNDS

Figure 1:
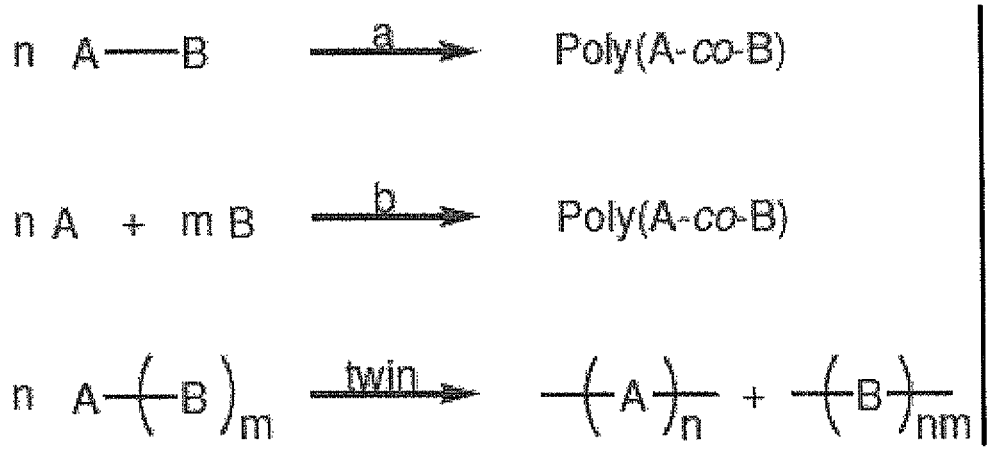

The invention relates to spiro compounds of the formula I and to composites prepared therefrom by twin ring-opening polymerisation, to porous metal oxide or semimetal oxide materials, which are preferably in the form of monoliths and are suitable, inter alia, for supporting catalysts.

The term "monolith" means that the majority of the material is in the form of a coherent piece whose dimensions are greater than those of conventional granules.

The term metal oxide or semimetal oxide here encompasses both metal oxides or semimetal oxides in the actual sense and also oxides which additionally comprise metal hydroxides or semimetal hydroxides (mixed oxides/hydroxides).

The cationic polymerisation of tetrafurfuryloxysilane (TFOS), as described in U.S. Pat. No. 2,276,094, produces, in only one step, a nanocomposite consisting of polyfurfuryl alcohol and silica gel crosslinked in an interpenetrating manner (see Spange et al. Angew. Chem. 2007, 119, 636-640).

Owing to the formation of two polymers from one monomer, the classification "twin polymerisation" has been proposed for this new type of polymerisation (see Spange et al. Angew. Chem. 2007, 119, 636-640). However, this classification is very general for the example presented by Spange et al. since it is a special condensation polymerisation, since the condensation product formed is water, which may become apparent in an interfering manner owing to possible side reactions caused by hydrolysis and as a component to be separated off. In particular if other elements from the Periodic System, such as aluminium or titanium, are employed in monomer combinations, the hydrolytic action of water is no longer negligible and results, simultaneously or dominantly, in conventional sol-gel process phenomena (see C. J. Brinker at al. *Sol-gel science: the physics and chemistry of sol-gel processing*, 6th Edn. Academic Press, San Diego, 1995).

Furthermore, furan derivatives are very reactive, making side reactions, in particular oxidation, easier, which makes the specific industrial use of such derivatives more difficult. Polyfuran resins are therefore often inhomogeneous, extremely brittle and coloured, often even black, which excludes many applications. The object of the present invention was therefore to further develop the known twin condensation polymerisation starting from TFOS and difurfuryloxy-dimethylsilane (DFS) in such a way that it results in uniform processes with no side reactions, no interfering substances, such as water, are eliminated in the course of the polymerisation, and that it results in uniform, colourless or only slightly coloured nanocomposites.

The present object is, surprisingly, achieved by the preparation of composites by "twin ring-opening polymerisation" of a metal or semimetal spiro compound, such as, for example, 2,2"-spirobi[4H-1,3,2-benzodioxasilyne] (abbreviated to SPISI). These composites have, for example, two bicontinuous, homogeneous and nanostructured phases comprising silica and phenolic resin, which can be converted into an oxidic monolith by oxidation of the organic phase without loss of the monolithic structure. The silica phase can likewise be dissolved out by etching, giving a continuous, porous organic resin body. Furthermore, if the reaction is carried out in a suitable manner, the composites obtained by the process according to the invention are uncoloured or only slightly coloured and transparent.

The present invention thus relates to spiro compounds of the formula I

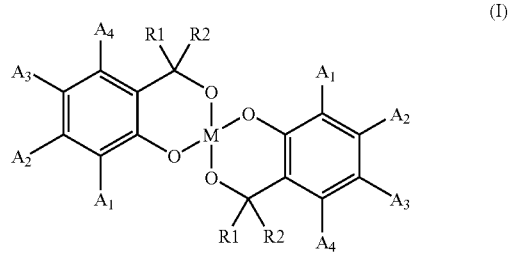

(I)

where
M is a metal or semimetal, preferably Si, Ti, Zr or Hf, particularly preferably Si or Ti,
$A_1, A_2, A_3, A_4$, independently of one another, are hydrogen or linear or branched, aliphatic hydrocarbon radicals, aromatic hydrocarbon radicals or aromatic-aliphatic hydrocarbon radicals,
R1, R2, independently of one another, are hydrogen or an alkyl group having 1 to 6 carbon atoms, preferably methyl or H.

It is preferred for two or more than two of the radicals $A_1$ to $A_4$ to be linked to one another, in particular fused, i.e. linked to form a common aromatic ring system.

It is furthermore preferred for one or more carbon atoms of the radicals $A_1$ to $A_4$ have been replaced, independently of one another, by heteroatoms, in particular by oxygen, sulfur and/or nitrogen. In addition, it is preferred for $A_1$ to $A_4$ to contain, independently of one another, one or more functional groups. Suitable functional groups are, in particular, the following groups: halogen, in particular bromine or chlorine, —CN and —NR$_2$, where R is, in particular, hydrogen or an aliphatic or aromatic hydrocarbon radical, preferably H, methyl, ethyl or phenyl.

In accordance with the invention, the radicals R1 and R2 are furthermore preferably, independently of one another, hydrogen or an alkyl group having 1 to 6 carbon atoms. $R_1$ and $R_2$ are preferably selected from hydrogen (H) and methyl. $R_1$ and $R_2$ are particularly preferably equal to H.

In addition, it is particularly preferred for at least one of the two radicals $A_1$ and $A_3$ to be a hydrogen atom. In a very particularly preferred embodiment, both $A_1$ and $A_3$ are a hydrogen atom. In addition, $A_1$ to $A_4$ are very particularly preferably equal to H.

The compound is most preferably 2,2'-spirobi[4H-1,3,2-benzodioxasilyne].

The present invention furthermore relates to an inorganic/organic hybrid material (composite) obtainable by polymerisation, preferably by twin ring-opening polymerisation, of one or more monomer units selected from the group of the spiro compounds of the general formula I

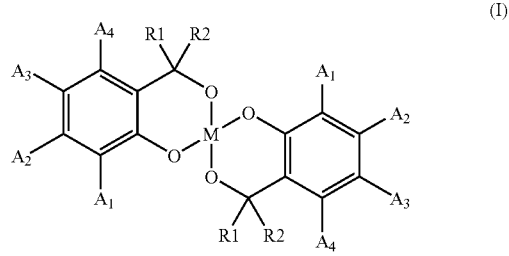

(I)

where $A_1$ and $A_3$ denote H, and/or compounds of the general formula II

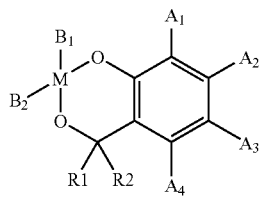
(II)

where
$B_1$ and $B_2$, independently of one another, are linear or branched aliphatic or aromatic hydrocarbon radicals, which may contain heteroatoms, preferably oxygen, nitrogen or sulfur, where ring closures may exist between the groups $B_1$ and $B_2$ via one or more carbon atoms or heteroatoms,
and M, $A_1$, $A_2$, $A_3$, $A_4$, R1, R2, have the meanings indicated above, where $A_1$ and $A_3$ are equal to hydrogen.

These composites can be employed, for example, as materials having high heat resistance and strength.

The present invention furthermore relates to a porous oxidic monolith obtainable from an inorganic/organic hybrid material by cationic polymerisation, preferably by twin ring-opening polymerisation, in which the organic phase is removed completely, preferably oxidised. These porous, stable, inorganic monoliths are suitable, for example, as catalyst supports.

In accordance with the invention, an "oxidic monolith" is defined as a monolith which consists of one or more metal oxides or semimetal oxides and may also comprise, as described above, metal hydroxides or semimetal hydroxides.

The present invention furthermore relates to a porous organic resin body obtainable from an inorganic/organic hybrid material by cationic polymerisation, preferably by twin ring-opening polymerisation, in which the inorganic phase is removed completely, preferably by dissolution or etching. Suitable solvents or etchants are preferably agents, in particular acids, which completely dissolve or chemically modify the inorganic phase without adversely affecting the organic phase.

These porous, stable, organic resins are suitable, for example, as catalyst supports or as supports for active substances, such as pharmaceuticals or crop-protection agents.

It is characteristic of the course of the twin polymerisation that two different macromolecules form simultaneously. The growth steps of the two polymers are kinetically coupled, so that the formation of the first polymer takes place on the same time scale as that of the second polymer. The twin polymerisation of organic/inorganic hybrid monomers is thus clearly distinguished from processes which are already known, such as simultaneous polymerisation, in which two different monomers are polymerised simultaneously in a single system, or consecutive polymerisation, where composite monomers (parent monomers) are often polymerised successively by two different mechanisms. A distinction is made in accordance with the invention between two types of twin polymerisation:

Hybrid monomers without ring equivalents must, even if they give two polymer structures in a single process, additionally form a further low-molecular-weight condensation product, such as, for example, water. This reaction is thus a condensation polymerisation.

The twin polymerisation according to the invention uses monomers with ring equivalents, which can form two polymers in a single process during a ring-opening polymerisation without low-molecular-weight products being formed. This is observed, for example, in the ring-opening, cationic polymerisation of spiro-silicon compounds.

The twin polymerisation of specifically conceived monomers, consisting of two different, covalently bonded units (hybrid monomers), results, in only one process step, in the simultaneous formation of two different polymers. For the purposes of the invention, it is crucial that two different macromolecular structures are formed simultaneously in a single process. The two polymers formed here may each form linear, branched or crosslinked structures. The molecular composition of the hybrid monomer defines the theoretical degree of crosslinking. If two crosslinked polymer structures form simultaneously, the length scale of the respective component in the composite is determined by the molecular size of the monomer unit and by diffusion processes. This novel polymerisation method thus also enables the development of nanostructured composites on the length scale from 0.5 nm to 2 nm for a very wide variety of material classes, where template-assisted processes using organic polymers come up against the intrinsic limit. The polymerisation method according to the invention thus closes the gap in the length scale between a molecule and a typical nanostructure <2 nm.

As already mentioned above, the advantageous bicontinuous structure, comprising an inorganic phase and an organic phase, of the hybrid material is achieved through the use of a single starting material, from which the two phases form simultaneously. The phases separate during the polymerisation without macroscopically visible precipitation of a reaction product occurring. Instead, the separation takes place on a length scale in the nanometre range. The two phases which form in the polymerisation interpenetrate completely and continuously. The formation of isolated domains cannot be observed if the reaction is carried out correctly.

Novel spiro compounds of the general formula I and/or compounds of the general formula II containing the radicals defined above, or combinations of the two formulae, avoid the formation of a low-molecular-weight elimination product during the reaction.

The hybrid materials formed are distinguished by a very homogeneous distribution of the two phases. The transparency of the resultant monoliths indicates that macroscopic domains of one of the two phases do not form in the reaction. The choice of a suitable acidic catalyst is also crucial for the optimum course of the polymerisation reaction. Preference is given here to the use of acids, such as, for example, trifluoroacetic acid or methanesulfonic acid. Relatively weak protonic acids, such as trifluoroacetic acid, which is particularly preferred, result in a slowed polymerisation reaction, giving transparent composites (see Table 1). By contrast, relatively strongly acidic catalysts often result in reactions which proceed uncontrollably quickly.

The invention furthermore relates to a process for the preparation of inorganic/organic hybrid material by polymerisation of one or more monomer units selected from the group of the spiro compounds of the general formula I and/or compounds of the general formula II, as indicated above.

For the formation of the inorganic/organic hybrid material, it is preferred for $A_1$ and $A_3$ in formula I and, if used, formula II to be hydrogen (H), in particular for $A_1$ to $A_4$ to be equal to H. Hydrogen atoms as substituents $A_1$ and $A_3$ represent reactive groups for the purposes of the polymerisation reaction.

The invention thus furthermore relates to a process for the production of oxidic monoliths, comprising the steps of:
 a) preparation of a hybrid material by polymerisation of one or more monomer units selected from the group of the spiro compounds of the general formula I and/or compounds of the general formula II, as defined above,
 b) complete removal of the organic phase, preferably by oxidation, to give an oxidic monolith.

In addition, the invention furthermore relates to a process for the production of porous organic resin bodies, comprising step a), as described above for the process for the production of oxidic monoliths, and the following step: preparation of a hybrid material by polymerisation of one or more monomer units, as described above under a), and complete removal of the inorganic phase, preferably by etching.

The present invention furthermore relates to a process for the preparation of spiro compounds of the formula I, characterised in that a compound of the formula III

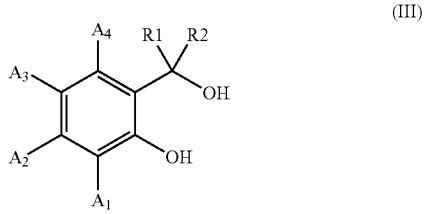

(III)

where $A_1, A_2, A_3, A_4$, R1, R2 have the meanings given above, where $A_1$ and $A_3$ are equal to H, is reacted with at least one alkoxy and/or halogen compound of the elements Si, Ti, Zr or Hf.

In accordance with the invention, the halogen compound employed is preferably $SiCl_4$ and the alkyl compound employed is preferably a tetraalkyl orthosilicate or tetraalkyl titanate. Particular preference is given to tetramethyl orthosilicate (TMOS) and tetraethyl orthosilicate as well as tetraisopropyl titanate.

In the case of the use of $SiCl_4$, triethylamine is used as auxiliary base. However, the bulky ammonium salt formed may represent a hindrance during work-up, meaning that the use of the tetraalkyl compounds is even more preferred.

The invention furthermore relates to the use of spiro compounds of the formulae I and/or II for the production of oxidic monoliths as catalyst supports.

The invention furthermore relates to the use of the inorganic or oxidic monoliths as catalyst supports. In this case, metals, oxides or complex compounds are either adsorbed on the porous surface or chemically bonded thereto. The favourable surface-to-volume ratio allows a large amount of catalyst per unit volume, the transport pores allow good material transport to the active centres, and the monolithic structure allows simple handling.

The invention furthermore relates to the use of spiro compounds of the formula I and/or II for the preparation of porous organic resins as catalyst supports or supports for active compounds, such as pharmaceuticals or crop-protection agents.

The invention furthermore relates to the use of the organic porous resins as catalyst supports or supports for active compounds. As catalyst supports, metals, oxides or complex compounds are either adsorbed on the porous surface or chemically bonded thereto. The favourable surface-to-volume ratio allows a large amount of catalyst per unit volume, and the transport pores allow good material transport to the active centres.

For supporting, active compounds are adsorbed in the pores and liberated in a controlled manner over time or depending on ambient variables. It is thus possible to liberate active compounds over a period of time or at the desired site of action.

The invention furthermore relates to the use of spiro compounds of the formulae I and/or II for the preparation of materials, in particular those having high heat resistance and strength.

The invention furthermore relates to the use of the composites as materials, in particular those having high heat resistance and strength.

The following examples are intended to illustrate the present invention. However, they should in no way be regarded as limiting. All compounds or components which can be used in the preparations are either known and commercially available or can be synthesised by known methods. The temperatures indicated in the examples are always in ° C. It furthermore goes without saying that, both in the description and also in the examples, the added amounts of the components in the compositions always add up to a total of 100%. Percentage data given should always be regarded in the given connection. However, they usually always relate to the weight of the part-amount or total amount indicated. Toluene and dichloromethane were dried.

EXAMPLES

Example 1

Figure 3:
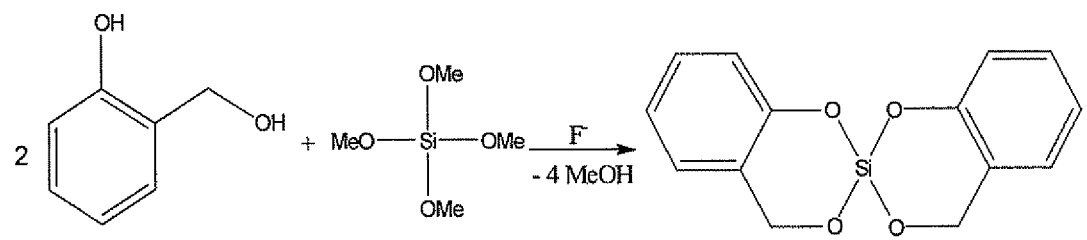

Preparation of 2,2'-spirobi[4H-1,3,2-benzodioxasilyne] (SPISI) (see FIG. 3)

135.77 g of salicyl alcohol (1.0937 mol) were dissolved in toluene at 85° C. 83.24 g (0.5469 mol) of tetramethoxysilane (TMOS) were subsequently slowly added dropwise, with 0.3 ml of tetra-n-butylammonium fluoride (1 M in THF) being injected in one portion after a third of the TMOS had been added. After stirring for one hour at 85° C., the methanol/toluene azeotrope was distilled off (63.7° C.). The remaining toluene was separated off in a rotary evaporator. The product was dissolved out of the resultant reaction bottom product using hexane at ≈70° C., and, after cooling, the clear solution was decanted off. After removal of the hexane, a white solid remains. The product can be purified further from impurities by re-precipitation using hexane.

$^1$H-NMR (400 MHz, CDCl$_3$, 25° C., TMS) δ [ppm]=5.21 (m, 4H, CH$_2$), 6.97-7.05 (m, 6H), 7.21-7.27 (M, 2H).

$^{13}$C-NMR (100 MHz, CDCl$_3$, 25° C.): δ [ppm]=66.3 (CH$_2$), 119.3, 122.3, 125.2, 125.7, 129.1, 152.4.

$^{29}$Si-CP-MAS (79.5 MHz): δ [ppm]=−78.4

Example 2

Figure 4:
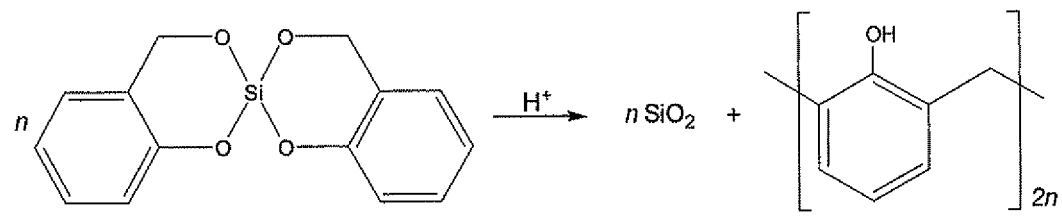

Cationic polymerisation (twin polymerisation) of 2,2'-spirobi[4H-1,3,2-benzodioxasilyne] to give the phenolic resin/silica nanocomposite (see FIG. 4)

The monomer prepared in accordance with Example 1 is melted under argon at 80° C. or dissolved in chloroform at 25° C. The initiator trifluoroacetic acid is added dropwise with stirring, and the reaction mixture is stirred at the same temperature for a further 3 h and subsequently left to stand at 25° C. The formation of the SiO$_2$ phase and of the phenolic resin is confirmed unambiguously by solid-state NMR spectroscopy.

Example 3

Oxidation to Nanoporous Silica

The composite monoliths are heated to 900° C. at 2 K/min with a supply of air and calcined at this temperature for 3 h.

Example 4

Production of a Porous Organic Resin Body

The composite materials are treated with a 20% solution of HF in water at 40° C. for 3 h.

Examples 5 to 11

Cationic Polymerisations of 2,2''-Spirobi[4H-1,3,2-Benzodioxasilyne] to give the Phenolic Resin/Silica Nanocomposite Under the Influence of the Catalysts Trifluoroacetic Acid (CF$_3$COOH) and Methanesulfonic Acid (CH$_3$SO$_3$H)

Example 7

Spiro Compound:Cat Ratio→25:1

72.920 g (0.268 mol) of 2,2'-spirobi[4H-1,3,2-benzodioxasilyne] were dissolved in 97 ml of CH$_2$Cl$_2$. 0.696 ml (1.029 g, 0.011 mol) of CH$_3$SO$_3$H dissolved in 73 ml of CH$_2$Cl$_2$ was added in one portion at 0° C. with stirring and reflux cooling. After 60 min, the cooling was discontinued; a pink solid had formed. The solid was subsequently dried in vacuo at 40° C.

Example 9

Spiro Compound:Cat. Ratio→25:1

14.856 g (0.055 mol) of 2,2'-spirobi[4H-1,3,2-benzodioxasilyne] were melted at 85° C., and 0.167 ml (0.249 g, 0.0022 mol) of CF$_3$CO$_2$H was added dropwise with stirring. The mixture was heated at 85° C. for a further 2 hours, but the stirring was discontinued after only one hour. An orange-brown transparent monolith was obtained.

INDEX OF FIGURES

FIG. 1: the schemes show that classical copolymerisations give copolymers: a) unimolecularly b) bimolecularly. In the case of twin polymerisation as a particular form of copolymerisation, two homopolymers (inorganic oxide and organic polymer) form simultaneously. A=inorganic component (Si, B, Ti, . . . ) B=organic component.

Figure 2:
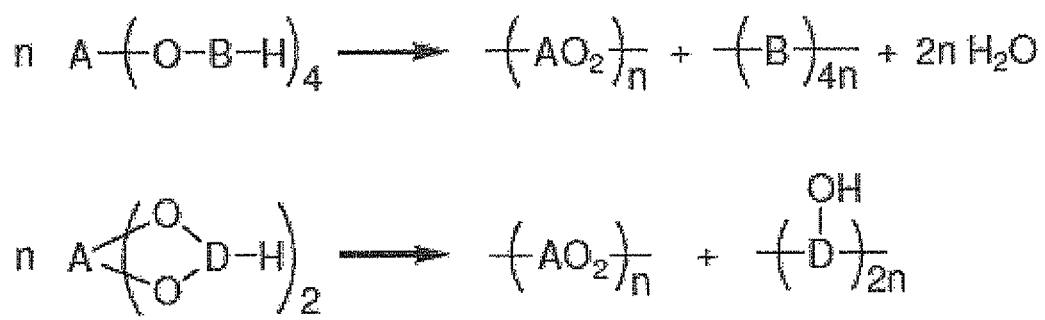

FIG. 2: shows twin polymerisations of the TFOS type and a specific spiro compound in accordance with the concept of the twin ring-opening polymerisation according to the invention. The organic component D here can carry two differently bonded oxygen atoms, which result in asymmetrical cleavage and form an OH-carrying polymer. Water-liberating condensation reactions are thus avoided.

FIG. 3: shows the synthesis of SPISI by esterification of salicyl alcohol using tetramethoxysilane.

FIG. 4: shows the theoretical overall equation of the twin ring-opening polymerisation according to the invention with reference to the example of 2,2'-spirobi[4H-1,3,2-benzodioxasilyne]. For simplification, only the formation of a linear polymer is shown. However, networks form in the polymerisation reaction according to the invention.

TABLE 1

| Spiro/cat.[a] | Reaction conditions | Reaction time; result |
| --- | --- | --- |
| 25 - CH$_3$SO$_3$H | 25° C., 3.09 mol l$^{-1}$/CH$_2$Cl$_2$ | 60 sec; polymerisation; pink solid |
| 50 - CH$_3$SO$_3$H | 25° C., 3.09 mol l$^{-1}$/CH$_2$Cl$_2$ | 5 min; inhomogeneous, partly transparent monolith |
| 25 - CH$_3$SO$_3$H[7] | 0° C., 1.58 mol l$^{-1}$/CH$_2$Cl$_2$ | 1 h, homogeneous pink powder |
| 10 - CF$_3$CO$_2$H | 85° C. melt | 30 min-1 h; transparent monolith |
| 25 - CF$_3$CO$_2$H[9] | 85° C. melt | 2 h, transparent monolith |
| 5 - CF$_3$CO$_2$H | 25° C., 3.09 mol l$^{-1}$/CH$_2$Cl$_2$ | 1 day; transparent monolith |
| 50 - CF$_3$CO$_2$H | 25° C., 3.09 mol l$^{-1}$/CH$_2$Cl$_2$ | 1 week; incomplete reaction, viscous |

[a]Spiro compound:catalyst molar ratio

[7],[9]Examples 7 and 9 described below

The invention claimed is:

1. A spiro compound of formula I

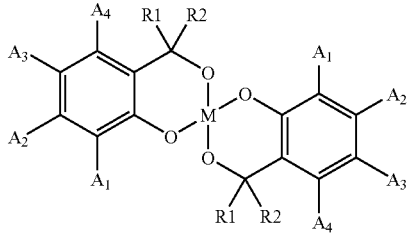

(I)

where
M is a metal or semimetal,
$A_1, A_2, A_3, A_4$, independently of one another, are hydrogen or linear or branched, aliphatic hydrocarbon radicals, aromatic hydrocarbon radicals or aromatic-aliphatic hydrocarbon radicals, and
R1, R2, independently of one another, are hydrogen or an alkyl group having 1 to 6 carbon atoms.

2. The spiro compound according to claim 1, wherein at least two of the radicals $A_1, A_2, A_3$ and $A_4$ are linked to one another.

3. The spiro compound according to claim 1, wherein one or more carbon atoms of the radicals $A_1, A_2, A_3$ and $A_4$ have been replaced, independently of one another, by heteroatoms.

4. The spiro compound according to claim 1, wherein $A_1, A_2, A_3$ and $A_4$ contain, independently of one another, one or more functional groups.

5. The spiro compound according to claim 1, wherein R1 and R2 denote H.

6. The spiro compound according to claim 1, wherein $A_1$ and $A_3$ denote H, $A_1$ to $A_4$ preferably denote H.

7. An inorganic/organic hybrid material obtainable by polymerization of one or more monomer units that is a spiro compound of formula I according to claim 1, where $A_1$ and $A_3$ are equal to H, and/or a compounds of formula II

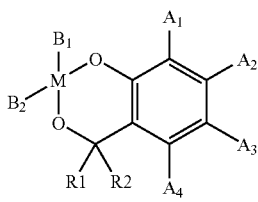

(II)

where
$B_1, B_2$, independently of one another, are linear or branched aliphatic or aromatic hydrocarbon radicals, which may contain heteroatoms, where ring closures exist between $B_1$ and $B_2$ via one or more carbon atoms or heteroatoms,
and $M, A_1, A_2, A_3, A_4$, R1, R2 have the meanings according to claim 1, where $A_1$ and $A_3$ are equal to hydrogen.

8. The inorganic/organic hybrid material according to claim 7, wherein the polymerization is a cationic polymerization.

9. A porous oxidic monolith obtainable from the inorganic/organic hybrid material according to claim 7, where a organic phase is removed completely.

10. A porous oxidic monolith according to claim 9, wherein the hybrid material comprises an inorganic, porous metal oxide or semimetal oxide framework and a polymer.

11. The porous oxidic monolith according to claim 10, wherein the metal oxide or semimetal oxide employed is silicon dioxide/hydroxide, titanium dioxide/hydroxide, zirconium dioxide/hydroxide or hafnium dioxide/hydroxide.

12. The porous Porous oxidic monolith according to claim 10, wherein the polymer is a phenolic resin.

13. A porous organic resin body obtainable from the inorganic/organic hybrid material according to claim 7 by completely removing the inorganic phase.

14. The porous organic resin body according to claim 13, wherein the hybrid material comprises an inorganic, porous metal oxide or semimetal oxide framework and a polymer.

15. The porous organic resin body according to claim 14, wherein the polymer is a phenolic resin.

16. A process for the preparation of inorganic/organic hybrid material by polymerization of one or more monomer units that are spiro compounds of formula I according to claim 1 and compounds of formula II

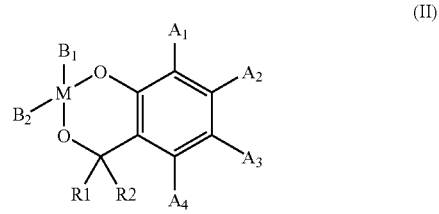

(II)

where
$B_1, B_2$, independently of one another, are linear or branched aliphatic or aromatic hydrocarbon radicals, which may contain heteroatoms, where ring closures exist between $B_1$ and $B_2$ via one or more carbon atoms or heteroatoms,
and $M, A_1, A_2, A_3, A_4$, R1, R2 have the meanings according to claim 1, where $A_1$ and $A_3$ are equal to hydrogen.

17. A process for the production of porous oxidic monoliths, comprising:
a) preparing a hybrid material by polymerizing one or more spiro monomer units of formula I according to claim 1 and compounds of formula II

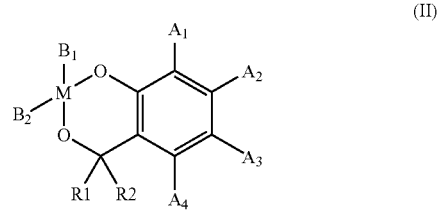

(II)

where
$B_1, B_2$, independently of one another, are linear or branched aliphatic or aromatic hydrocarbon radicals, which may contain heteroatoms, where ring closures exist between $B_1$ and $B_2$ via one or more carbon atoms or heteroatoms,
and $M, A_1, A_2, A_3, A_4$, R1, R2 have the meanings according to claim 1, where $A_1$ and $A_3$ are equal to hydrogen.
b) complete removal of an organic phase.

18. A process for the preparation of spiro compounds of formula I according to claim 1, comprising reacting a compound of formula III

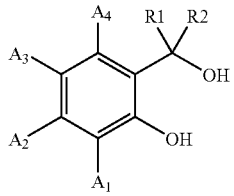

(III)

where $A_1$, $A_2$, $A_3$, $A_4$, $R_1$, $R_2$ have the meanings according to claim 1 and where $A_1$ and $A_3$ are equal to H, is reacted with at least one alkyl and/or halogen compound of Si, Ti, Zr or Hf.

19. The process according to claim 18, wherein the alkyl compounds employed are tetraalkyl orthosilicates or tetraalkyl titanates.

20. A process for the production of porous organic resin bodies, comprising:
   a) preparing a hybrid material by polymerizing one or more spiro monomers of formula I according to claim 1 and compounds of formula II

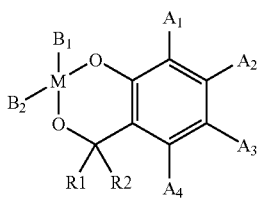

(II)

where
$B_1$, $B_2$, independently of one another, are linear or branched aliphatic or aromatic hydrocarbon radicals, which may contain heteroatoms, where ring closures exist between $B_1$ and $B_2$ via one or more carbon atoms or heteroatoms,
and M, $A_1$, $A_2$, $A_3$, $A_4$, R1, R2 have the meanings according to claim 1, where $A_1$ and $A_3$ are equal to hydrogen
   b) complete removal of an inorganic phase.

21. A method comprising using spiro compounds of the formula I according to claim 1 and/or compounds of the formula II

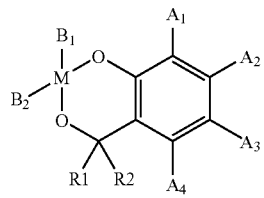

(II)

where
$B_1$, $B_2$, independently of one another, are linear or branched aliphatic or aromatic hydrocarbon radicals, which may contain heteroatoms, where ring closures exist between $B_1$ and $B_2$ via one or more carbon atoms or heteroatoms,
and M, $A_1$, $A_2$, $A_3$, $A_4$, R1, R2 have the meanings according to claim 1, where $A_1$ and $A_3$ are equal to hydrogen for the production of porous organic resin bodies for use as catalyst supports or as supports for active compounds.

22. A method comprising using spiro compounds of the formula I according to claim 1 and/or compounds of the formula II

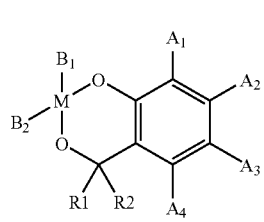

(II)

where
$B_1$, $B_2$, independently of one another, are linear or branched aliphatic or aromatic hydrocarbon radicals, which may contain heteroatoms, where ring closures exist between $B_1$ and $B_2$ via one or more carbon atoms or heteroatoms,
and M, $A_1$, $A_2$, $A_3$, $A_4$, R1, R2 have the meanings according to claim 1, where $A_1$ and $A_3$ are equal to hydrogen for the production of porous oxidic monoliths for use as catalyst supports.

* * * * *

UNITED STATES PATENT AND TRADEMARK OFFICE
CERTIFICATE OF CORRECTION

PATENT NO. : 8,460,628 B2
APPLICATION NO. : 12/810765
DATED : June 11, 2013
INVENTOR(S) : Matthias Koch et al.

It is certified that error appears in the above-identified patent and that said Letters Patent is hereby corrected as shown below:

In the Claims

Column 10, line 8, claim 12 reads "The porous Porous", should read --The porous--.

Signed and Sealed this
First Day of October, 2013

Teresa Stanek Rea
*Deputy Director of the United States Patent and Trademark Office*